(12) United States Patent
Cheng et al.

(10) Patent No.: US 8,994,932 B2
(45) Date of Patent: Mar. 31, 2015

(54) MULTIMODAL PLATFORM FOR NONLINEAR OPTICAL MICROSCOPY AND MICROSPECTROSCOPY

(75) Inventors: Ji-Xin Cheng, West Lafayette, IN (US); Hongtao Chen, Los Angeles, CA (US); Mikhail Slipchenko, West Lafayette, IN (US); Haifeng Wang, Singapore (SG)

(73) Assignee: Purdue Research Foundation, West Lafayette, IN (US)

( * ) Notice: Subject to any disclaimer, the term of this patent is extended or adjusted under 35 U.S.C. 154(b) by 862 days.

(21) Appl. No.: 13/141,039

(22) PCT Filed: Dec. 18, 2009

(86) PCT No.: PCT/US2009/006691
§ 371 (c)(1),
(2), (4) Date: Jul. 13, 2011

(87) PCT Pub. No.: WO2010/071682
PCT Pub. Date: Jun. 24, 2010

(65) Prior Publication Data
US 2011/0261349 A1 Oct. 27, 2011

Related U.S. Application Data

(60) Provisional application No. 61/139,570, filed on Dec. 20, 2008.

(51) Int. Cl.
*G01N 21/00* (2006.01)
*G01N 21/64* (2006.01)
(Continued)

(52) U.S. Cl.
CPC .............. *G01N 21/6486* (2013.01); *G01J 3/44* (2013.01); *G01N 21/636* (2013.01); *G01N 21/6458* (2013.01); *G01N 21/65* (2013.01); *G01N 2021/653* (2013.01); *G02B 21/16* (2013.01)
USPC .......................................................... 356/72

(58) Field of Classification Search
CPC ....... G01N 21/65; G01N 2021/653; G01J 3/10
USPC .......................................................... 356/301
See application file for complete search history.

(56) References Cited

U.S. PATENT DOCUMENTS 5,815,262 A 9/1998 Schrof et al.
5,898,717 A 4/1999 Yin
(Continued)

FOREIGN PATENT DOCUMENTS

DE 10 2007 021 378 A1 * 11/2008 ............. G01N 21/65

OTHER PUBLICATIONS

Barad, Y., et al., "Nonlinear Scanning Laser Microscopy by Third Harmonic Generation", Applied Physics Letters, vol. 70, Feb. 24, 1997, pp. 922-924.
(Continued)

*Primary Examiner* — Kara E Geisel
(74) *Attorney, Agent, or Firm* — Lee & Hayes, PLLC; Christopher J. White

(57) ABSTRACT

A method for providing images using a multimodal nonlinear optical microscope is disclosed. The method includes providing a foundation femtosecond laser beam, generating a first femtosecond laser beam and a second femtosecond laser beam corresponding to the foundation femtosecond laser beam, combining the first femtosecond laser beam and the foundation femtosecond laser beam to generate a first combination femtosecond laser beam, and generating a coherent anti-Stokes Raman scattering (CARS) signal based on the first combination femtosecond laser beam. A multimodal nonlinear optical microscopy platform is also disclosed.

19 Claims, 10 Drawing Sheets

(51) Int. Cl.
*G01J 3/44* (2006.01)
*G01N 21/65* (2006.01)
*G02B 21/16* (2006.01)
*G01N 21/63* (2006.01)

(56) References Cited

U.S. PATENT DOCUMENTS

| | | | |
|---|---|---|---|
| 6,020,591 | A | 2/2000 | Harter et al. |
| 6,521,899 | B1 | 2/2003 | Wolleschensky |
| 6,798,507 | B2 | 9/2004 | Xie et al. |
| 6,809,814 | B2 | 10/2004 | Xie et al. |
| 7,403,282 | B2 | 7/2008 | Silberberg et al. |
| 7,436,501 | B2 | 10/2008 | Hashimoto et al. |
| 2006/0063188 | A1* | 3/2006 | Zanni et al. ............... 435/6 |
| 2006/0238745 | A1 | 10/2006 | Hashimoto |
| 2007/0088219 | A1 | 4/2007 | Xie et al. |
| 2007/0247620 | A1 | 10/2007 | Koo |
| 2010/0046039 | A1* | 2/2010 | Xie et al. ............ 356/301 |
| 2010/0177307 | A1* | 7/2010 | Rimke et al. ............ 356/301 |

OTHER PUBLICATIONS

Campagnola, Paul and Loew, Leslie, "Second-harmonic Imaging Microscopy for Visualizing Biomolecular Arrays in Cells, Tissues and Organisms", Nature Biotechnology, vol. 21, No. 11, Nov. 2003, pp. 1356-1360.

Cheng, Ji-Xin, et al., "An Epi-Detected Coherent Anti-Stokes Raman Scattering (E-CARS) Microscope With High Spectral Resolution and High Sensitivity", The Journal of Physical Chemistry B, vol. 105, Feb. 7, 2001, pp. 1277-1280.

Cheng, Ji-Xin and Xie, X. Sunney, "Coherent Anti-Stokes Raman Scattering Microscopy: Instrumentation, Theory and Applications", J. Phys. Chem. B, pp. 827-840, 2004.

Denk, W., et al., "Two-photon Laser Scanning Fluorescence Microscopy", Science, vol. 248, pp. 73-76, 1990.

Evans, Conor, et al., "Chemical Imaging of Tissue in vivo With Video-Rate Coherent Anti-Stokes Raman Scattering Microscopy", PNAS, vol. 102, pp. 16807-16812, Nov. 15, 2005.

Fu, Yan, et al., "Coherent Anti-Stokes Raman Scattering Imaging of Myelin Degradation Reveals a Calcium-Dependent Pathway in Lyso-PtdCho-Induced Demyelination", J Neurosci Res, vol. 85, pp. 2870-2881, Oct. 2007.

Fu, Yan, et al., "Second Harmonic and Sum Frequency Generation Imaging of Fibrous Astroglial Filaments in Ex Vivo Spinal Tissues", Biophysical Journal, vol. 92, pp. 3251-3259, May 2007.

Ganikhanov, Feruz, et al., "Broadly Tunable Dual-Wavelength Light Source for Coherent Anti-Stokes Raman Scattering Microscopy", Optics Letters, vol. 31, pp. 1292-1294, May 2006.

Hellerer, Thomas, et al., "Monitoring of Lipid Storage in Caenorhabditis Elegans Using Coherent Anti-Stokes Raman Scattering (CARS) Microscopy", PNAS, vol. 104, pp. 14658-14663, 2007.

Huang, Shaohui, et al., "Two-Photon Fluorescence Spectroscopy and Microscopy of NAD (P)H and Flavoprotein", Biophysical Journal, vol. 82, pp. 2811-2825, May 2002.

Moger, Julian, et al., "Imaging Metal Oxide Nanoparticles in Biological Structures With CARS Microscopy", Optics Express, vol. 16, pp. 3408-3419, Mar. 2008.

Nan, Xiaolin, et al., "Vibrational Imaging of Lipid Droplets in Live Fibroblast Cells With Coherent Anti-Stokes Raman Scattering Microscopy", Journal of Lipid Research, vol. 44, pp. 2202-2208, 2003.

Squier, Jeff, et al., "Third Harmonic Generation Microscopy", Optics Express, vol. 3, pp. 315-324, Oct. 1998.

Wang, Han-Wei, et al., "Label-Free Imaging of Arterial Cells and Extracellular Matrix Using a Multimodal CARS Microscope", Science Direct, pp. 1813-1822, 2008.

Wang, Li Li Haifeng and Cheng, Ji-Xin, "Quantitative Coherent Anti-Stokes Raman Scattering Imaging oof Lipid Distribution in Coexisting Domains", Biophysical Journal, vol. 89, pp. 3480-3490, Nov. 2005.

Zipfel, Warren, et al., "Live Tissue Intrinsic Emission Microscopy Using Muliphoton-Excited Native Flourescence and Second Harmonic Generation", PNAS, vol. 100, pp. 7075-7080, Jun. 2003.

Yelin, D., and Silberberg, Y, Laser Scanning Third-Harmonic-Generation Microscopy in Biology, Optics Express, vol. 5, pp. 169-175, Oct. 1999.

Vogler, N, et al., "CARS Microscopy for Biomedical Imaging", Institute of Physical Chemistry, Friedrich-Schiller-University Jena.

Zhou, Yaopeng, et al., "Adaptive Optics Two-Photon Fluorescence Microscopy", MEMS Adaptive Optics, edited by Scot S. Olivier, et al., Proc. of SPIE vol. 6497 (2007).

International Searching Authority, International Search Report, mailed Jun. 29, 2010 (PCT/US2009/006691).

International Searching Authority, Written Opinion of the International Searching Authority, mailed Jun. 29, 2010 (PCT/US2009/006691).

* cited by examiner

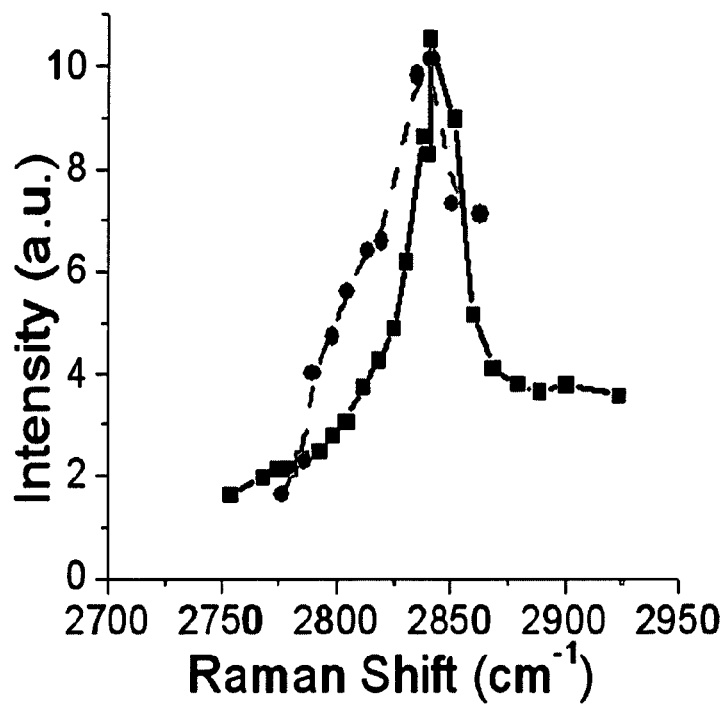
FIG. 2e
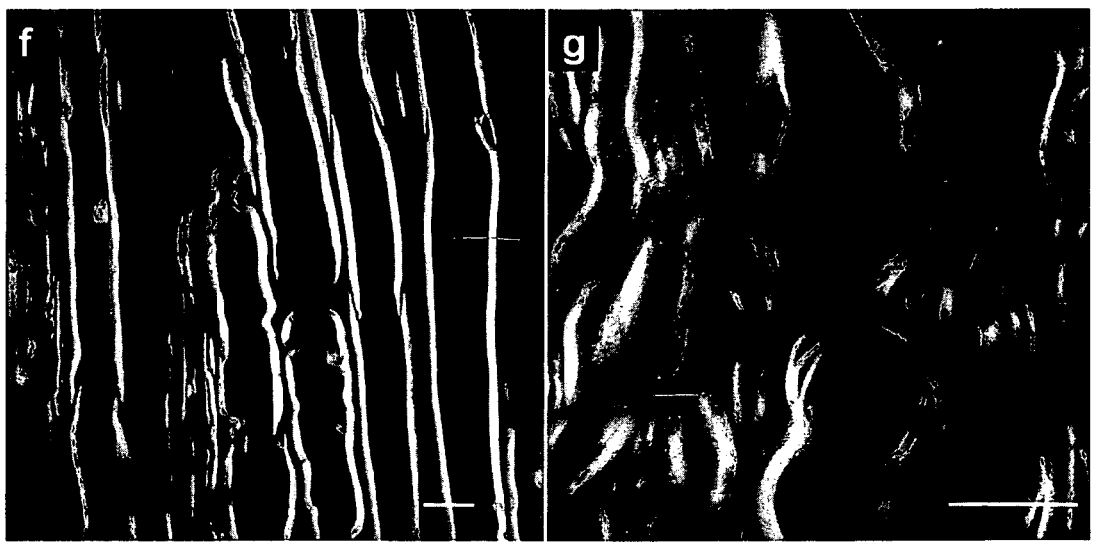
FIG. 2f                    FIG. 2g

US 8,994,932 B2

MULTIMODAL PLATFORM FOR NONLINEAR OPTICAL MICROSCOPY AND MICROSPECTROSCOPY

PRIORITY

The present application is related to, claims the priority benefit of, and is a U.S. §371 national stage entry of, International Patent Application Serial No. PCT/US2009/006691, filed Dec. 18, 2009, which is related to, and claims the priority benefit of U.S. Provisional Patent Application Ser. No. 61/139,570, filed Dec. 20, 2008. The contents of each of these applications are hereby incorporated by reference in their entirety into this disclosure.

This invention was made with government support under grant number EB007243 awarded by the National Institutes of Health. The United States Government has certain rights in the invention.

TECHNICAL FIELD

The present invention relates generally to microscopy, and more particularly, to optical microscopy and microspectroscopy.

BACKGROUND

Understanding the interactions between cells, extracellular matrix, and stromal molecules in a tissue environment is an emerging frontier of biology. While such interactions are new, providing images of biological tissues is a time-honored endeavor in the field of biology. An optical microscope, i.e., a type of microscope which uses visible light and a series of lenses to magnify images of small objects, cannot provide sufficient information needed by researchers and clinicians about a host of biological tissues. Accordingly, special nonlinear optical microscopic techniques have been developed for different modalities for imaging complex tissue samples with inherent 3D spatial resolution requirements. Normally laser beams are used to excite tissue samples in different modalities. Some modes of nonlinear optical microscopy involve a single laser beam for excitation of the biological tissue. While other modes involve multiple beams. Single beam modalities include Two-Photon Fluorescence (TPF) microscopy, Second Harmonic Generation (SHG), and Third Harmonic Generation (THG) microscopy. TPF and SHG can be integrated with a single femtosecond (fs) laser. THG microscopy has also been combined with SHG and TPF by using an Optical Parametric Oscillator (OPO) system.

Coherent anti-Stokes Raman Scattering (CARS) microscopy is another nonlinear optical imaging technique that facilitates high-speed vibrational imaging of molecules. As a two-beam modality, CARS microscopy is mostly operated with picosecond (ps) pulses, either from two synchronized Ti:sapphire lasers or from a synchronously pumped OPO system. In comparison with fs pulses, ps pulse excitation not only provides sufficient spectral resolution, but also increases the ratio of resonant signal to nonresonant background.

Recently, CARS, TPF, and sum-frequency generation (SFG) modalities have been integrated into a microscope operated with ps pulses for multimodal imaging of white matter and arterial tissue. Although tunable ps laser systems operating in the near infrared (NIR) range are widely accepted for high-speed CARS imaging, the reduced efficiency of non-linear optical (NLO) process caused by longer pulse duration hinders the application of ps lasers to TPF and SHG imaging. While, a key advantage of the fs laser source is its superior image capabilities of TPF, SHG, and THG imaging over ps lasers, CARS microscopy has traditionally been performed with ps laser systems.

Therefore, a practical and efficient solution to fully utilizing all NLO imaging capabilities is therefore needed.

SUMMARY

A method for providing images using a multimodal nonlinear optical microscope is disclosed. The method includes providing a foundation femtosecond laser beam, generating a first femtosecond laser beam and a second femtosecond laser beam corresponding to the foundation femtosecond laser beam, combining the first femtosecond laser beam and the foundation femtosecond laser beam to generate a first combination femtosecond laser beam, and generating a coherent anti-Stokes Raman scattering (CARS) signal based on the first combination femtosecond laser beam.

The method also includes generating a two-photon fluorescence (TPF) signal based on the foundation femtosecond laser beam.

The method also includes generating a two-photon fluorescence (TPF) signal based on the foundation femtosecond laser beam.

The method further includes combining the second femtosecond laser beam with the first combination femtosecond laser beam to generate a second combination femtosecond laser beam, and generating a polarization-sensitive coherent anti-Stokes Raman scattering (PCARS) signal based on the second combination femtosecond laser beam.

The method further includes generating a second harmonic generation (SHG) signal based on the second femtosecond laser beam.

The method further includes generating a third harmonic generation (THG) signal based on the second femtosecond laser beam.

The method also includes generating the second femtosecond laser beams using an Optical Parametric Oscillator (OPO).

The foundation laser beam in the method has a wavelength number of about 790 nm, the first femtosecond laser beam has a wavelength number of about 2036 nm, and the second femtosecond laser beam has a wavelength number of about 1290 nm.

The method further includes doubling the frequency of the first femtosecond laser beam to generate a third femtosecond laser beam.

The method further includes generating the third femtosecond laser beam using a periodically poled lithium niobate (PPLN) crystal-based doubler.

The method further includes, adjusting polarization of the foundation femtosecond laser beam and polarization of the second femtosecond laser beam corresponding to polarization of the third femtosecond laser beam.

BRIEF DESCRIPTION OF THE DRAWINGS

The foregoing aspects and other features of the present disclosure are explained in the following description, taken in connection with the accompanying drawings.

FIG. 2e is a graph of CARS spectra of subcutaneous fat recorded with fs (grey) and ps (black) lasers.

FIG. 2f is an epi-detected CARS image of myelin sheath surrounding parallel axons in a fresh spinal tissue.

FIG. 2g is an epi-detected CARS image of myelin sheath surrounding parallel axons in a paranodal myelin at a node of Ranvier.

FIG. 4c is a forward-detected CARS image of lipid droplets in liver cells in the same tissue of FIG. 4a.

FIGS. 5a-5f show three-beam Polarization Sensitive CARS (PCARS) imaging of C-D bonds.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1A:
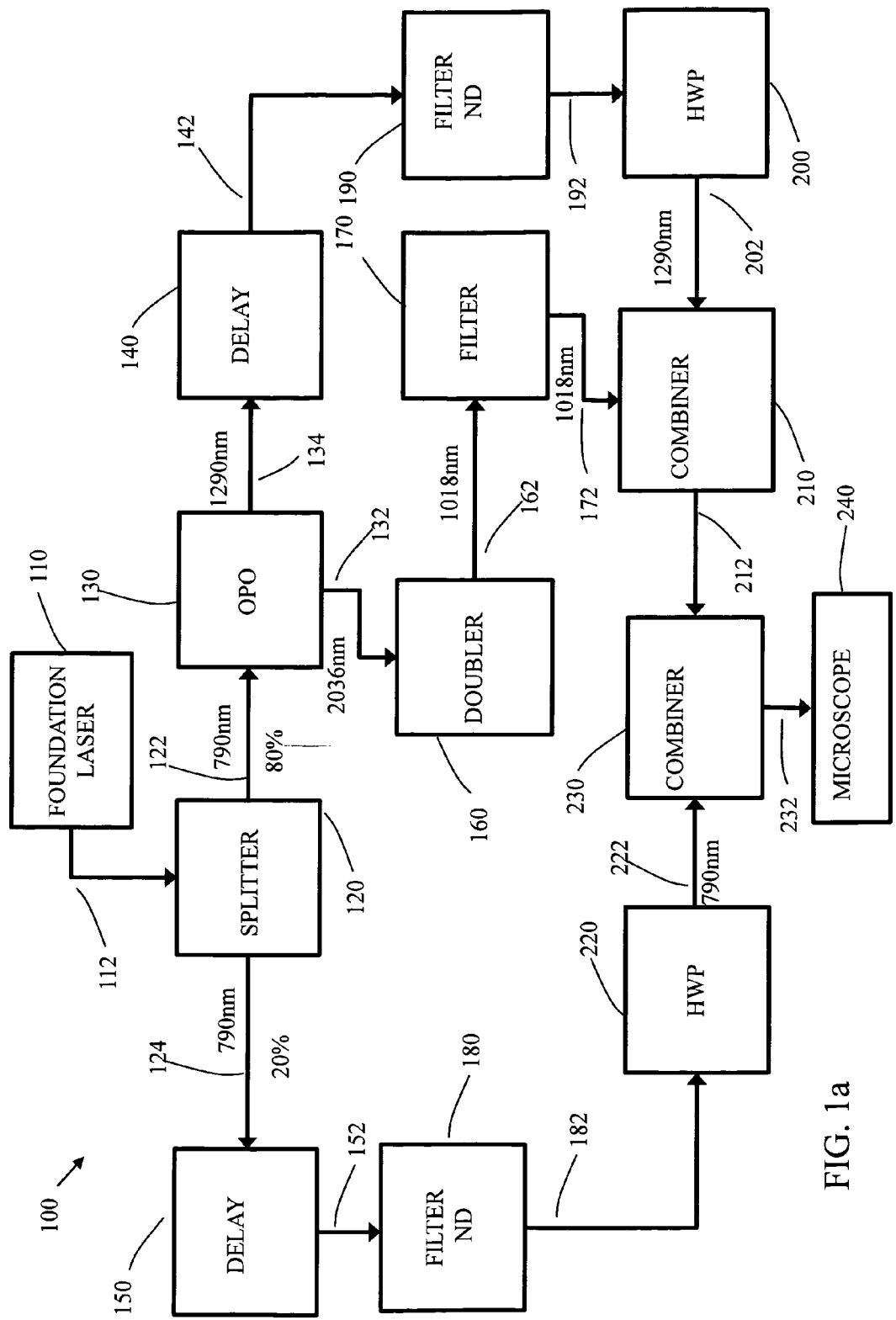
FIG. 1a is a schematic of a multimodal NLO microscope using a common femtosecond (fs) laser source.

Referring to FIG. 1a, a block diagram for a nonlinear multimodal platform for optical Microscopy and Microspectroscopy 100 is provided. The system 100 of FIG. 1a includes a foundation laser beam generator 110, a splitter 120, an Optical Parametric Oscillator (OPO) 130, a delay element 140, a delay element 150, a frequency doubler 160, and a filter 170. The system 100 further includes a Neutral Density (ND) filter 180, another ND filter 190, a Half Wave Plate (HWP) 200, a combiner 210, another HWP 220, and another combiner 230. The system 100 also includes a microscope 240.

The foundation laser 110 is operable coupled to the splitter 120 which splits the laser beam into two outputs 122 and 124 of varying powers. The output 122 is operably divided by the OPO 130 into two output laser beams of varying wavelengths 132 and 134. The output 132 is processed by a frequency doubler 160 which produces the output 162. The output 162 is filtered by the filter 170, which provides an output 172. Also, the output 124 is delayed by the delay element 140 to produce an output 142. The output 142 is filtered by the ND filter 190 which produces the output 192. The output 192 is operably coupled to the HWP 200 to produce an output 202. The outputs 172 and 202 are combined by the combiner 210 to produce a combination laser beam 212. Also, the output 124 is delayed by the delay element 150 to produce an output 152. The output 152 is filtered by the ND filter 180 to produce an output 182. The output 182 is operably coupled to the HWP block 220 to produce an output 222. The combination laser beam 212 and the output 222 are combined to produce a combination laser beam 232 which is an input to the microscope 240.

The platform of FIG. 1a provides capabilities for Coherent Anti-stokes Raman Scattering (CARS), Polarization sensitive CARS (PCARS), Second Harmonic Generation (SHG), Third Harmonic Generation (THG), and Two-Phonon Fluorescence (TPF) imaging modalities. A femtosecond (fs) laser 110 provides a foundation laser source for the above modalities. The terms foundation and pump laser are used interchangeably and are intended to convey the same concept. An example of the fs laser 110 is a Mai Tai laser from Spectra-Physics which provides an output laser 112 at a wavelength of 790 nm at 3.0 W. The splitter 120 is provided to split the output 112 of the fs laser source 110 into two beams. The beam 122 has about 80% of the power of the output 112 of the laser source 110 and the other beam 124 has about 20%. The 80% beam 122 is provided as an input to an Optical Parametric Oscillator (OPO) 130 to generate two outputs 132 and 134 with lower frequencies than the input. The sum of the frequencies of the outputs 132 and 134 is equal to the frequency of the input 122. The input 122 of the OPO 130 is commonly referred to as the "pump" while one output 132 is commonly referred to as the "idler" and the other output 134 is commonly referred to as the "signal." The idler output 132 has a wavelength of 2036 nm and the signal output 134 has a wavelength of 1290. An example of the OPO 130 is an Opal-BB from Spectra-Physics.

For synchronization purposes, the signal output 134 and the 20% output of the splitter 124 are passed through optical delay elements 140 and 150, respectively. The optical delay elements 140 and 150 provide delayed outputs 142 and 152, respectively. The idler output 132 is provided as an input to the frequency doubler 160. The frequency doubler 160 can be a Periodically Poled Lithium Niobate (PPLN) crystal-based doubler. The frequency doubler 160 provides an output 162 which has a wavelength 1018 nm. The output 162 is also referred to as the Stokes laser. The output 162 is filtered by a colored glass filter 170 which provides the filtered output 172. An example of the filter 170 is RG 850 manufactured by Schott. The delayed 20% beam 152 is also filtered by the neutral density filter 180 which provides the filtered output 182. Further, the delayed signal 142 output from the delay element 140 is filtered by the neutral density filter 190 which produces the filtered output 192. The filtered output 192 is applied to the HWP 200 for altering the polarization state of the filtered output 192 which travels through the half wave plate 200, i.e., for polarization rotation to be used in PCARS. The half wave plate 200 produces an output 202. The filtered output 172 and the output 202 are combined by the combiner 210 to generate a collinearly combined combination laser beam 212 of 1290 nm and 1080 nm beams. The filtered output 182 is also applied to the HWP 220 which provides an output 222. The combination laser beam 212 and the output 222 are combined by the combiner 230 to produce the collinearly generated combination laser beam 232. The default polarizations of 790 nm, 1018 nm and 1290 nm beams are vertical before the microscope. The combination laser beam 232 is used as an input for platform microscope such as a flow view 1000 confocal microscope manufactured by Olympus.

Figure 1B:
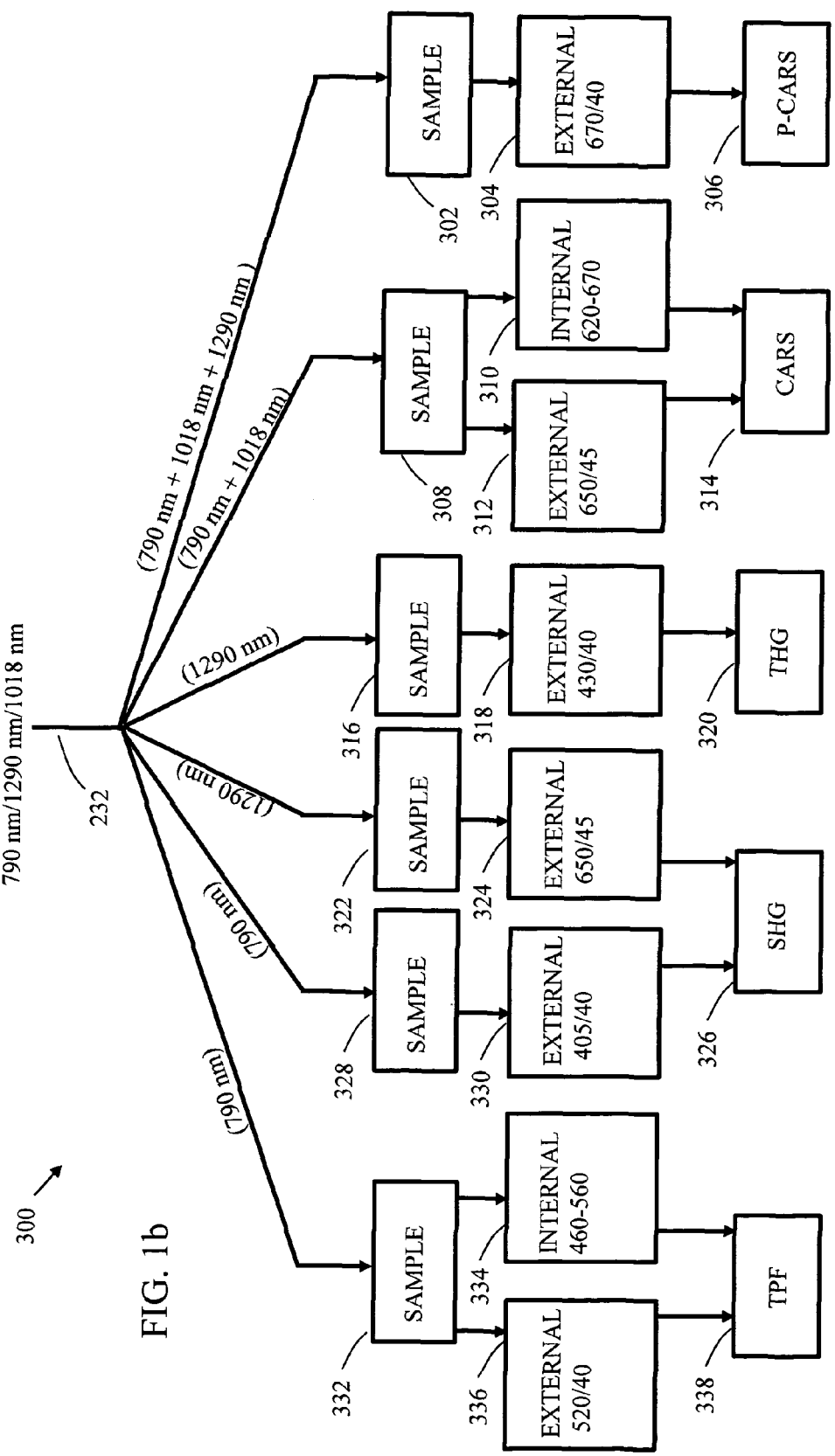
FIG. 1b is a flow diagram for different modalities.
Figure 2A:
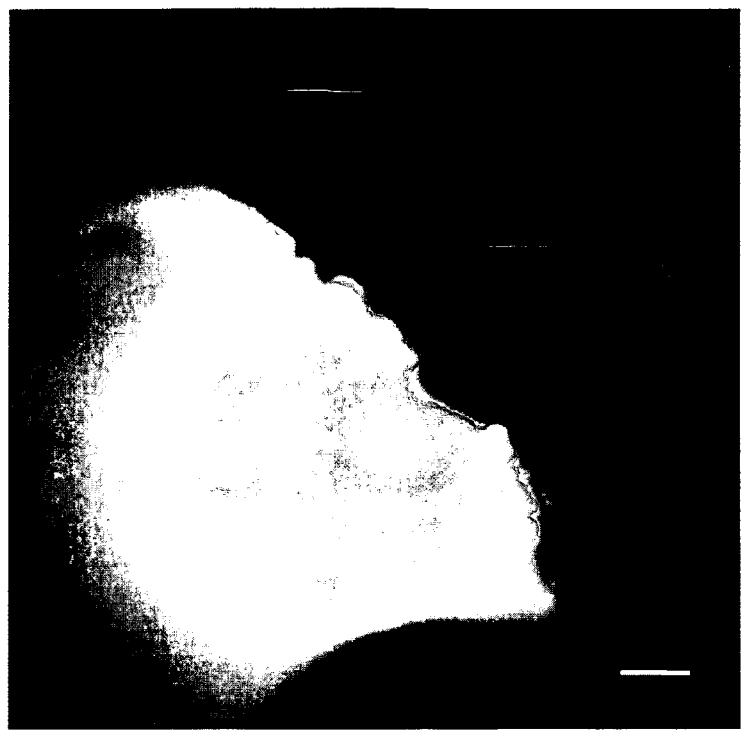
FIGS. 2a-2b are vibrational contrast forward-detected Coherent anti-Stokes Raman Scattering (CARS) images of C—H rich objects of a subcutaneous fat tissue produced by fs lasers.
Figure 2B:
Figure 2C:
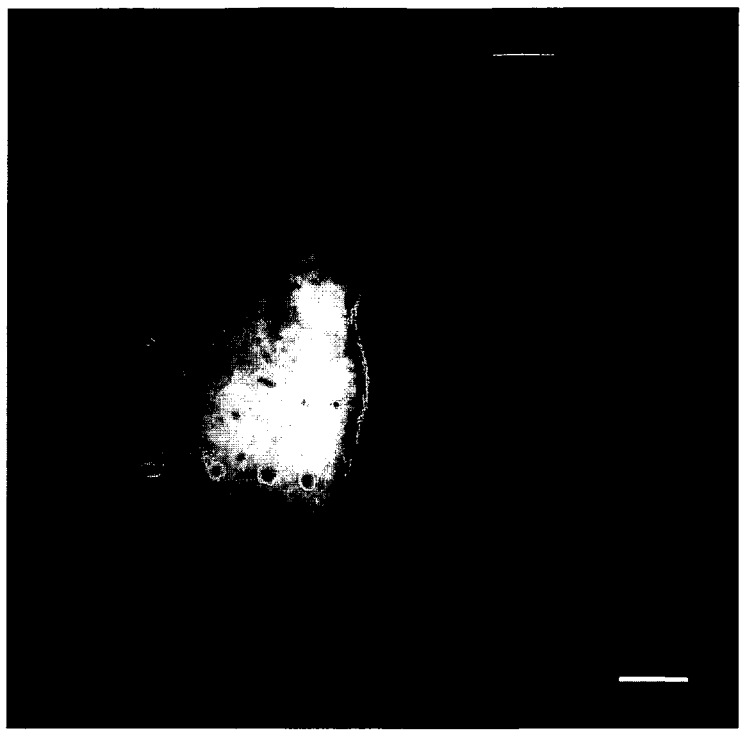
FIGS. 2c-2d are vibrational contrast forward-detected CARS images of C—H rich objects of a subcutaneous fat tissue produced by ps lasers.
Figure 2D:
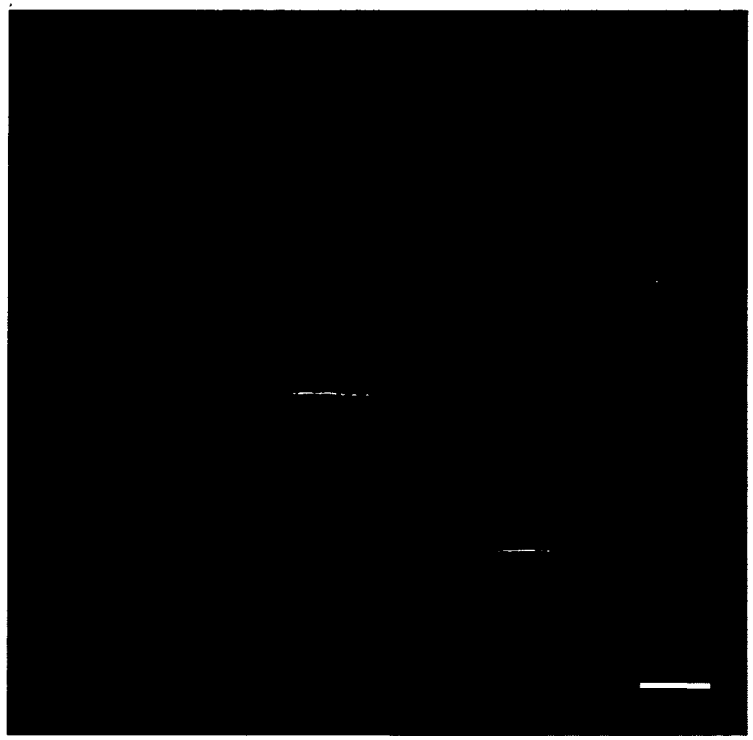

Referring to FIG. 1b, a flow diagram 300 for the nonlinear multimodal platform of FIG. 1a is depicted. The combination laser beam 232 having three wavelengths 790 nm, 1290 nm, and 1018 nm is provided as the output of the combiners 230, as shown in FIG. 1a. The combination laser beam 232 is provided to the microscope 240 as a source of excitation for a variety of different tissues and imaging modalities appropriate for the tissues. By placing a particular tissue in the microscope 240 and applying a particular optical bandpass filter between the tissue and detectors of the microscope 240, a particular wavelength can be targeted which has excited the tissue. Combinations of bandpass filters and the combination laser beam 232 can therefore result in a particular modality. In addition to optical bandpass filters, electronic bandpass filters can be used internal to the microscope 240. Therefore, the combination laser beam 232 is shown with different branches. On each branch, a wavenumber is provided inside parentheses. It should be appreciated that the wavenumber and bandpass filter combinations are provided as exemplary implantations. Therefore, other combinations can also be achieved. It should also be appreciated that a tissue that is placed in the microscope 240 receives all the components of the combination laser beam 232. For example a tissue with florescence qualities may be excited with the combination laser beam 232, however, the 790 nm wavelength component of the combination laser beam 232 excites the tissue in a TPF regime. Placing the appropriate bandpass filter between the tissue and the microscope detector targets the wavelength of the optical signal that the tissue emits in the TPF modality. In FIG. 1b, this bandpass filter is shown as the external 520/40 bandpass filter 336 or the internal 460-560 filter 334.

A sample 302 is exposed to the combination laser beam 232. Using a bandpass filter 304 the sample 302 can be imaged using PCARS microscopy 306. An example of the bandpass filter 304 is an external 670/40 bandpass optical filter, i.e., a bandpass filter centered at 670 nm and a bandpass of 40 nm. A sample 308 is exposed to the combination laser beam 232. Using bandpass filters 310 and 312, the sample 308 can be imaged using CARS microscopy 314. An example of the bandpass filters 310 and 312 are an external 650/45 bandpass filter, i.e., a bandpass filter centered at 650 nm and a bandpass of 45 nm, and an internal digital bandpass filter 620-670 nm filter, i.e., a bandpass filter centered at 645 nm and a bandpass of 50 nm.

A sample 316 is exposed to the combination laser beam 232. Using a bandpass filter 318 the sample 316 can be imaged using THG microscopy. An example of the bandpass filter 318 is an external 430/40 bandpass filter, i.e., a bandpass filter centered at 430 nm and a bandpass of 40 nm.

A sample 322 is exposed to the combination laser beam 232. Using a bandpass filter 324 the sample 322 can be imaged using SHG microscopy 326. An example of the bandpass filter 324 is an external 650/45 bandpass filter, i.e., a bandpass filter centered at 650 nm and a bandpass of 45 nm.

Alternatively, a sample 328 is exposed to the combination laser beam 232. Using a bandpass filter 330 the sample 328 can be imaged using the SHG microscopy 326. An example of the bandpass filter 330 is an external 405/40 bandpass filter, i.e., a bandpass filter centered at 405 nm and a bandpass of 40 nm. Samples 322 and 328 are image in the alternative, i.e., either sample 322 is imaged or sample 328, but not both. A sample 332 is exposed to the combination laser beam 232. Using bandpass filter 334 and 336 the sample 332 can be imaged using TPF microscopy 328. An example of the bandpass filter 334 is an internal 450 nm-560 nm bandpass filter, i.e., a digital bandpass filter centered at 505 nm with a bandpass of 110 nm. An example of the bandpass filter 336 is an external 520/40 bandpass filter, i.e., a bandpass filter centered at 520 nm and a bandpass of 40 nm.

A 60×/CARS water objective with a 1.2 numerical aperture (1-U2B893IR, Olympus) was used to focus all laser beams into a specimen. Backward signal was collected by the same objective and detected by either embedded internal spectral detectors or an external detector. An example of an internal detector is a Grating spectrometer with a photomultiplier tube (PMT). An example of an External detector is a R7683 from Hamamatsu Photonics. Forward signal was collected by an air condenser and detected by a second external PMT detector. An example of an air condenser is an Olympus 0.55 NA air condenser. Proper bandpass filters were used to selectively transmit a certain NLO signal. The acquisition time for each frame of 512×512 pixels is 1.1 seconds.

For CARS imaging of lipids, the pump laser ($\omega_1$) at 790 nm (12658 cm$^{-1}$) 110 and the Stokes laser ($\omega_2$) at 1018 nm (9823 cm$^{-1}$) 172 provide a wavenumber difference centered at 2840 cm$^{-1}$ that matches the Raman shift of symmetric $CH_2$ stretch vibration in lipids. CARS signal at 645 nm was detected by external detectors with the 650/45 nm bandpass filter 312 or by an internal spectral detectors with the 620-670 nm filter 310. Backward SHG signal was detected by an external detector with the 650/45 nm bandpass filter 324 for 1290 nm excitation. THG signal was detected with the 430/40 nm bandpass filter 318 for 1290 nm excitation. Two-photon excited auto fluorescence was detected by an external detector with the 520/40 bandpass filter 336 or by an internal spectral detector with the 460-560 nm spectral filter 334 for 790 nm excitation. An internal lambda-scan mode was used for microspectroscopy analysis within 400-700 nm range. Images were analyzed using FluoView software (Olympus America Inc., PA) and Image J (NIH). Maximum average power of the 790 nm beam was 220 mW before (222) the microscope 240. The power of the 2036 nm beam 132 was 240 mW before PPLN crystal. PPLN crystal produced a 1018 nm beam with a power of 52 mW before (172) the microscope 240 and 2.2 mW at the sample. Maximum power of 1290 nm beam was 400 mW before (202) microscope 240. 790 nm and 1290 nm beams were attenuated by microscope optical components and neutral density wheels to 10 to 20 mW and 2 to 18 mW at the sample, respectively. No noticeable photo-damage to samples was observed during these experiments.

To evaluate spatial resolution of the imaging system 100, $TiO_2$ nanoparticles were used due to their high third-order nonlinear susceptibilities and intense CARS signal. $TiO_2$ nanoparticles with 50~100 nm diameter were spread on a coverslip and covered by water. Media 1 and Media 2 are epi-detected CARS and THG z-stack movies of $TiO_2$ nanoparicles. The movies were obtained with 0.05 μm step size and the size was 21 μm×21 μm. Typical full width at half maximum (FWHM) of the lateral and axial intensity profiles of a single particle is 0.38 μm and 1.11 μm for CARS imaging. Typical FWHM of the lateral and axial intensity profiles of a single particle is 0.49 μm and 1.35 μm for THG imaging. Spatial resolution of CARS imaging is lower than previously reported 0.28 μm and 0.75 μm obtained by two synchronized picoseconds (ps) lasers at shorter wavelengths. On the other hand, a longer wavelength provides an improved penetration depth, which benefits tissue study.

$TiO_2$ nanopowder (<100 nm) was purchased from Sigma-Aldrich (St. Louis, Mo.) for estimation of spatial resolution. 10 mg nanopowder was mixed with 1 mL milliQ water and sonicated for 5 min. After sonication, 20 μL mixture was dropped on a coverslip and dried in air. A drop of water was added to cover the dried nanopowder before imaging. Subcutaneous fat extracted from a Long Evans rat was used to evaluate vibrational contrast and spectral resolution. The fat tissue was maintained in Dulbecco's Modified Eagle Medium (DMEM) medium at 37° C. DMEM is suitable for most types of cells, including human, monkey, hamster, rat, mouse, chicken, and fish cells. A small piece of fat tissue was placed in a coverslip-bottomed dish (MatTek, Ashland, Mass.) with 100 μL medium and a coverslip was placed on top to fix the position of fat tissue before imaging. Fresh spinal cord ventral white matter was extracted from adult guinea pigs as previous described. The ventral white matter was cut into 1-cm long strips and placed in a coverslip-bottomed dish and subsequently incubated in fresh Krebs' solution at room temperature for 1 h prior to imaging. Fresh liver tissues were explanted from C57BL/6J background mice fed high fat diet for 3 weeks. A slice of fresh tissue was placed in a coverslip-bottomed dish with 100 µL medium before imaging. For live cell imaging, KB cells were cultured in a coverslip-bottomed dish using a Roswell Park Memorial Institute medium (RPMI1640). KB cells belong to a cell line derived from human carcinoma of the nasopharynx. RPMI, is a form of medium used in cell culture and tissue culture. It has traditionally been used for growth of Human lymphoid cells. This medium contains a great deal of phosphate and is formulated for use in a 5% carbon dioxide atmosphere.

Vibrational contrast and spectral resolution are two important parameters for CARS microscopy. Pulses of a few ps provide high vibrational contrast and good spectral resolution for CARS imaging because their spectral width matches the typical Raman band (8-10 $cm^{-1}$). Pulses of ~100 fs duration have a bandwidth of ~150 $cm^{-1}$ approximately in the NIR region, thus most energy is used for generation of nonresonant background. However, some biologically significant Raman bands have a broad spectral profile. For instance, the $CH_2$ stretch vibration at 2850 $cm^{-1}$ has a line width of ~50 $cm^{-1}$. For C—H rich objects, pulses of larger spectral width could give a good contrast. To compare the performance of ps and fs pulses, the CARS spectra of fat tissues was recorded by the fs CARS system as well as a traditional picoseconds CARS setup. Forward-detected CARS images on- and off-CH vibration are shown in FIG. 2a-2d. The Raman shift is marked in each image. The scale in bars is 20 µm. A strong vibrational contrast was observed with either fs or ps lasers. The spectral width obtained by the fs system (FIG. 2e, gray) is broader than that by the ps system (FIG. 2e, black) as expected. Meanwhile, both systems generated the same vibration contrast of 6:1 measured as the ratio of the resonant signal at ~2840 $cm^{-1}$ to nonresonant background at 2760 $cm^{-1}$. This result demonstrates the applicability of fs lasers to acquire high-quality CARS images of lipid-rich features.

To further demonstrate the feasibility of fs CARS for vibrational imaging of lipid membranes, myelin sheath has been imaged which is an extended plasma membrane wrapping around an axon and is crucial for impulse conduction. CARS microscopy has been proved as a unique tool for visualization of myelin in healthy and diseased states. FIG. 2f showed that high quality CARS images of myelin can be obtained with the fs laser source. The signal to background ratio of 9:1 is comparable to the value (15:1) obtained with ps lasers. Moreover, high spatial resolution allowed clear visualization of paranodal myelin loops around a node of Ranvier (FIG. 2g). The scale of FIGS. 2f-2g in bars is 10 µm.

Figure 3A:
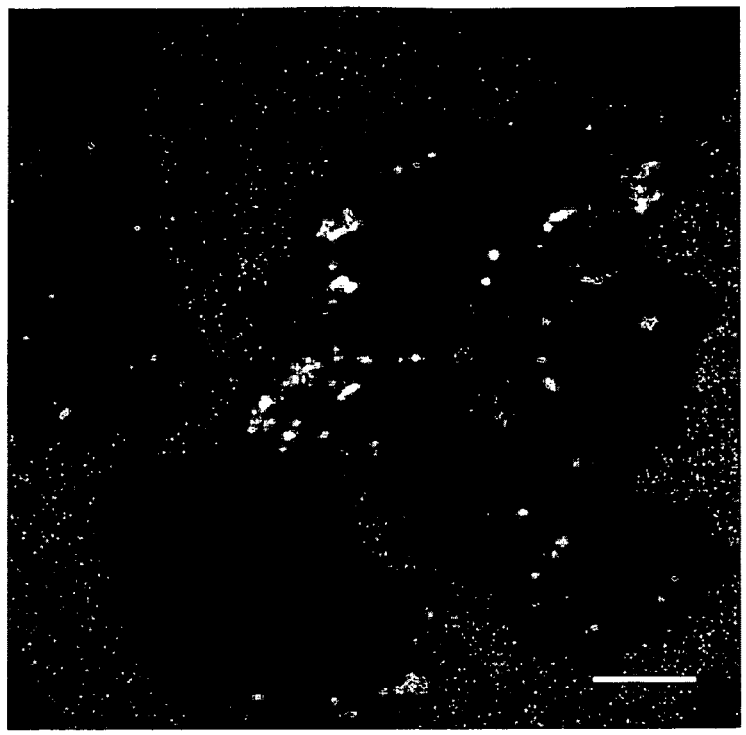
FIG. 3a is a forward-detected Third Harmonic Generation (THG) image of lipid droplets inside live KB cells.
Figure 3B:
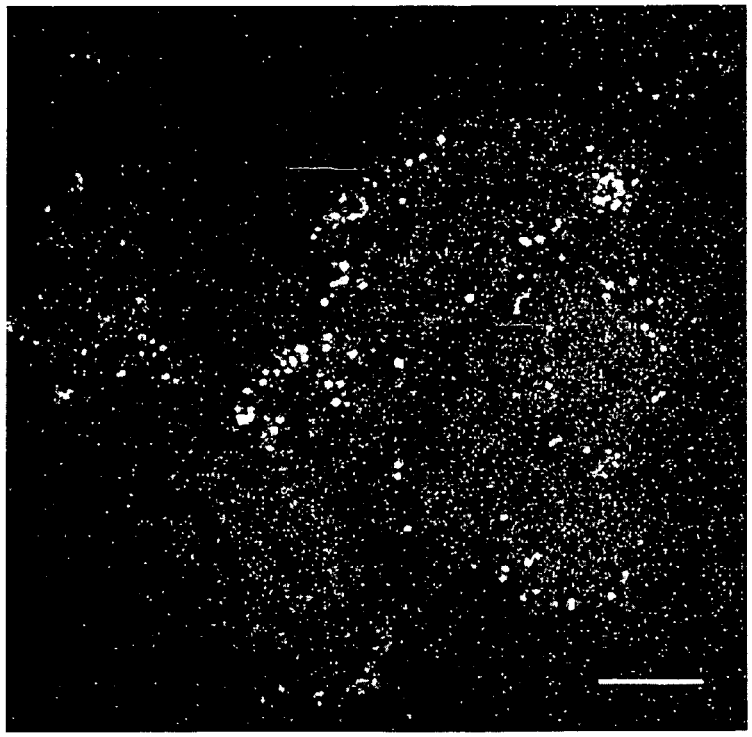
FIG. 3b is a forward-detected CARS image of lipid droplets inside live KB cells.

Lipid droplets can be imaged by CARS as well as THG microscopy in a label-free manner. The system 100 allowed direct comparison of these two modalities using live cells. A 1290 nm excitation was used to produce forward THG signal from lipid droplets inside KB cells (FIG. 3a). A 790 nm beam and a 1018 nm beam were used to produce forward CARS signal from the same cells (FIG. 3b). The scale in bars in FIGS. 3a and 3b is 10 µm. The laser powers used for CARS and THG imaging were adjusted so that the peak intensities from lipid droplets were at the same level. For THG imaging, the final power at the sample was 18 mW, while for CARS imaging, the pump power was 1.7 mW and the Stokes power was 1.4 mW. Based on these data, CARS signal was approximately $18^3/(3 \times 1.7^2 \times 1.4) = 480$ times stronger than the THG signal, where 3 is the combinatorial factor. The larger CARS signal is conceivably due to Raman enhancement. Additionally, the Gouy phase shift of a focused beam, which diminishes NLO signal generation from a focal volume, was tripled in THG but partially canceled in CARS. Because of the Gouy phase shift, THG imaging is not sensitive to homogeneous medium, thus a dark contrast from the rest of the cells was observed. In contrast, forward CARS signal also arose from the solvent and the entire cell body was visualized.

As discussed above, a key advantage of the fs laser source is its superior capabilities of TPF, SHG, and THG imaging over ps lasers. To illustrate such advantage, fresh liver tissues were imaged using TPF to visualize intrinsic fluorphores, SHG to visualize collagen, and CARS to visualize lipid bodies in hepatocytes. Backward TPF signals and forward CARS signals were collected simultaneously, whereas TPF and backward SHG were recorded sequentially.

Figure 4A:
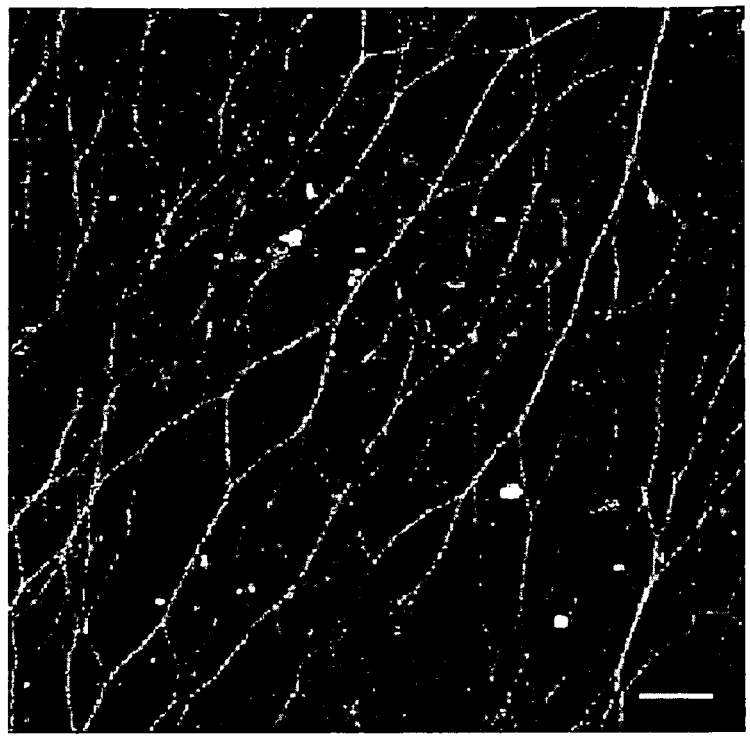
FIG. 4a is a Two-Photon Fluorescence (TPF) image of a fresh liver tissue excited at 790 nm and detected in the 450-550 nm region.
Figure 4B:
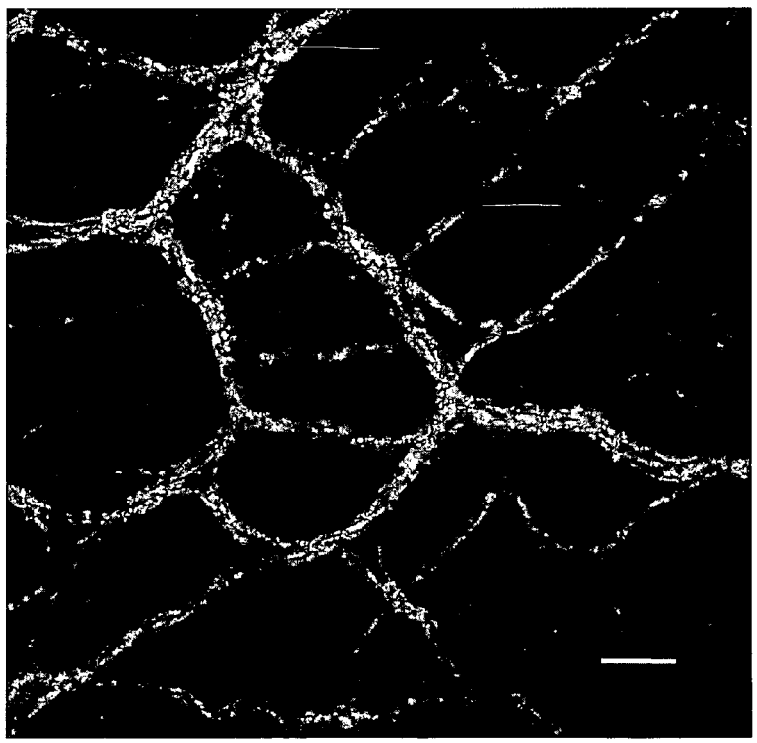
FIG. 4b is a Second Harmonic Generation (SHG) image of collagen fibers in the same liver tissue of FIG. 4a at 1290 nm excitation.
Figure 4C:
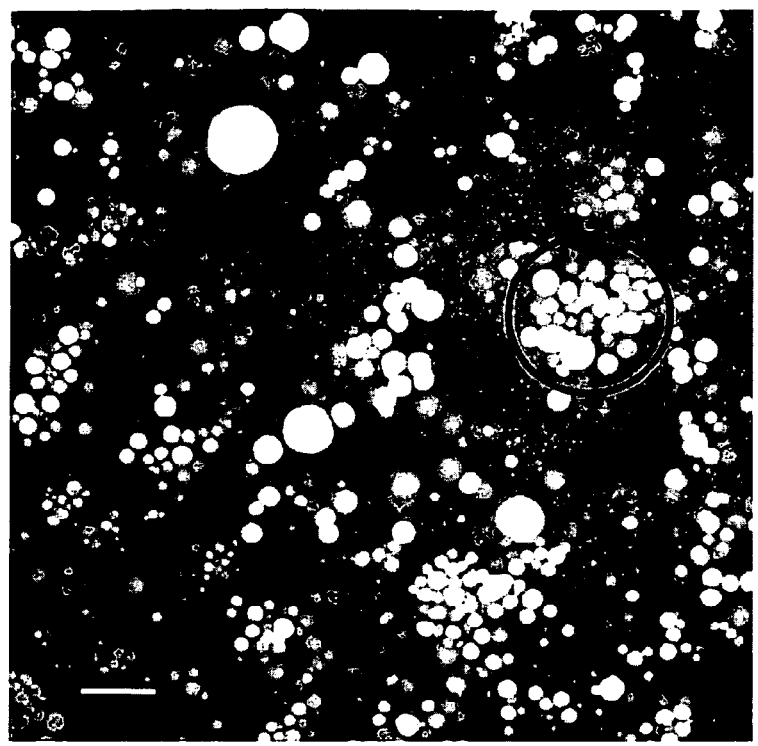
Figure 4D:
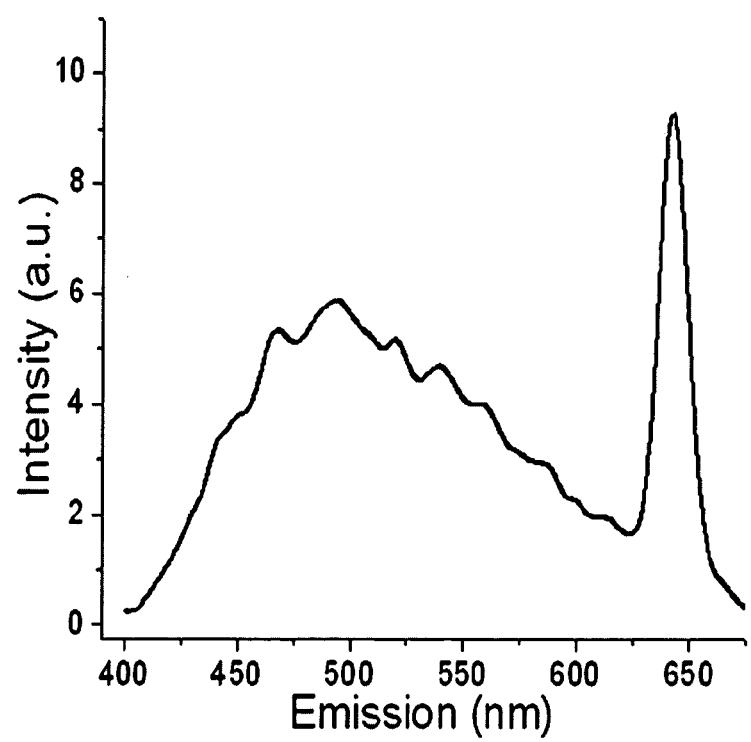
FIG. 4d is a microspectroscopy of the circled area shown in FIG. 4c using a λ-scanner detector utilizing the same lasers.
Figure 4E:
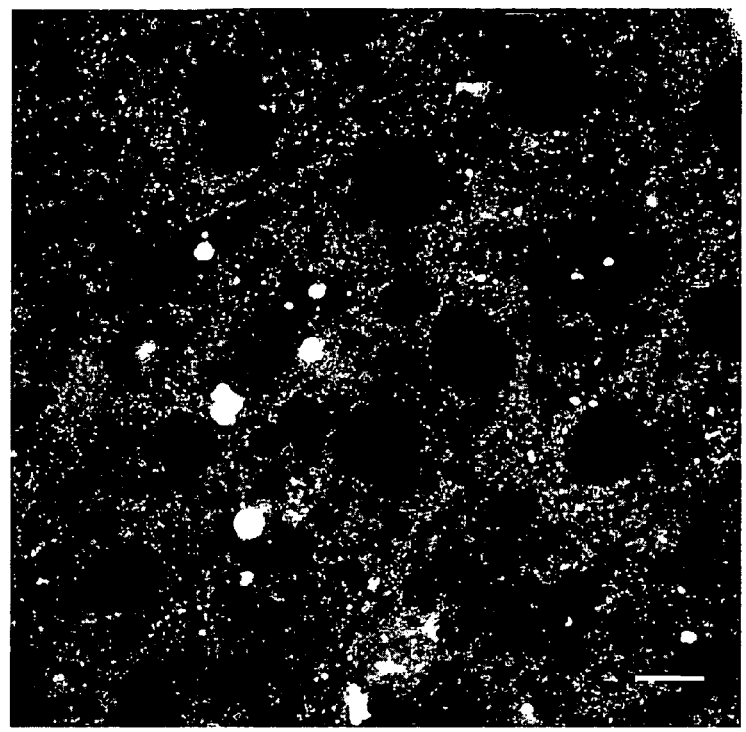
FIG. 4e is a two-photon autofluorescence image excited by the 790 nm laser.
Figure 4F:
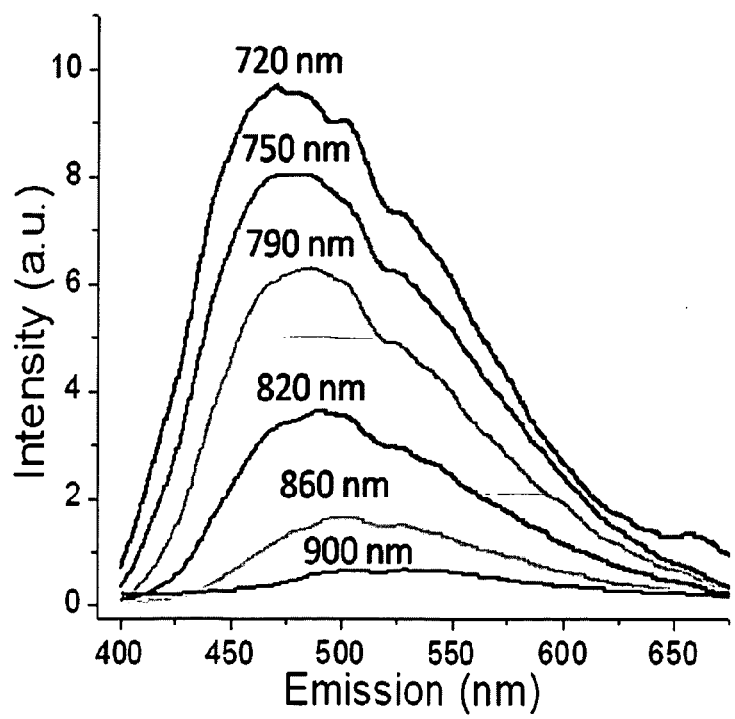
FIG. 4f is a two-photon autofluorescence emission spectra excited at different wavelengths from 720 nm to 900 nm.

At the liver surface, a strong TPF signal from fibrous structures was observed (z=0 µm, FIG. 4a). The scale in bars in FIGS. 4a-4c and 4e is 10 µM. When the laser was focused into the tissue around 1 µm above the surface, collagen fibers were observed clearly by SHG imaging with 1290 nm excitation. Although the 790 nm excitation can provide similar information of collagen fibers, the 1290 nm beam provides better penetration depth and higher selectivity by minimizing the autofluorescence from hepatocytes. When the laser was focused into the tissue around 4 to 5 µm above the surface, numerous lipid droplets inside cells were visualized by CARS (FIG. 4c). The two-photon excited autofluorescence of the same liver cells was visualized simultaneously (FIG. 4e). Media 3 shows a typical z-stack movie of TPF (green), SHG (cyan) and CARS (gray) imaging of a fresh liver tissue. Movies were obtained with 1 µm step size and the size was 210 µm×210 µm. In addition to multimodal imaging, the system 100 is capable of multimodal spectral analysis with a lambda-scanner. By performing lambda-scan of the circled area in FIG. 4c, a spectrum that contains auto fluorescence from liver cells and CARS signal from intracellular lipid bodies was obtained and shown in FIG. 4d. The CARS signal peaked at 645 nm and the autofluorescence peaked around 490 nm are shown in FIG. 4d. To assign the origin of autofluorescence, spectra at different excitation wavelengths from 720 nm to 900 nm were recorded and observed the strongest autofluorescence at 720 nm excitation (FIG. 4f). Based on the excitation spectra of coenzymes, it was determined that autofluorescence signal mainly arose from NAD(P)H. This multimodal spectral analysis can be used to study the relationship between lipid accumulation and metabolic activity in liver cells.

Figures 5D, 5E, 5F:
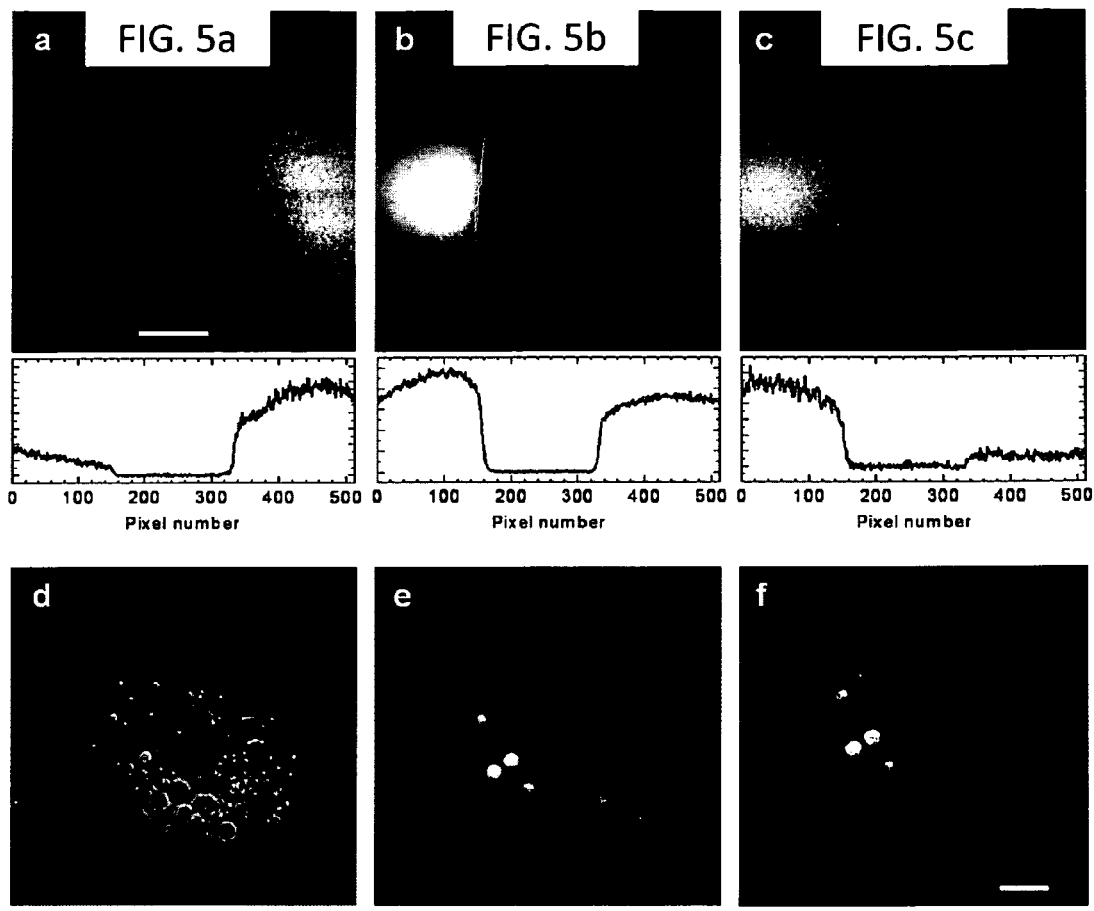

Although two-beam CARS allows selective imaging of CH-rich objects as shown above, vibrational imaging of weaker Raman bands is often hindered by a nonresonant background that arises from both the objects and the surrounding medium. Theoretically it was shown that the CARS signal is inherently background free if the polarizations of the three excitation beams are properly aligned. Using the fs laser platform 100, a novel three-beam polarization CARS for background-free vibrational imaging of deuterated molecules is provided. The linearly polarized 790 nm, 1018 nm, and 1290 nm beams were collinearly combined and temporally overlapped. With parallel polarization, a bright contrast from a glycerol drop was observed using the resonant CARS signal produced by the 790 nm and 1018 nm beams (FIG. 5a). However, the CARS signal from the deuterated glycerol drop was accompanied by a strong nonresonant background from glycerol drop (FIG. 5b), although the wavenumber difference between the 1018 nm and the 1290 nm beam is resonant with C-D stretch vibration around 2100 cm$^{-1}$. By adjusting the polarizations of the 790 nm and the 1290 nm beam relative to the 1018 nm beam, the nonresonant background from glycerol was minimized and the deuterated glycerol drop was selectively visualized (FIG. 5c). The polarization angle is about 60 degree for the 790 nm beam relative to the 1018 nm beam and is about 60 degrees for the 1290 nm beam relative to the 1018 nm beam. Quantitatively, the resonant signal was reduced by 10 times and the nonresonant background was suppressed by 200 times, resulting in an improvement of contrast by 20 times. This approach permitted high-speed vibrational imaging of deuterated lipids inside live cells. In 3T3-L1 cells fed d31-palmitic acid, deuterated lipid bodies as well as background from the solvent using three-beam CARS with parallel polarization (FIG. 5e) were visualized. With polarization CARS, the nonresonant background was suppressed and only the lipid bodies were detected (FIG. 5f).

Laser sources have been essential for the advances in CARS microscopy. In 1980s, visible dye lasers with non-collinear beam geometry were used in the first CARS microscope. In 1999, Xie and coworkers revived this technique by using two synchronized near infrared fs pulse trains for CARS imaging in a collinear beam geometry. Later, Hashimoto et al., used an amplified laser system to produce two ps pulse trains for CARS imaging. Cheng et al. indicated for the first time that tunable ps lasers operating in the NIR wavelengths not only provides high spectral resolution, but also provide superior vibrational contrast over fs lasers. In the spectral domain, the spectral width of an fs pulse is much broader than the width of most Raman lines, i.e., vibrational line widths are typically on the order of 10 cm$^{-1}$ whereas fs pulses are more than 100 cm$^{-1}$ in bandwidth. On the other hand, the spectral width of a ps pulse matches the Raman line width, thus focusing the excitation energy on a single Raman band and permitting high-speed CARS imaging. Since then, ps laser sources have been widely used in developments of CARS microscopy, including electronically synchronized Ti:sapphire lasers and synchronously pumped, intracavity-doubled ps OPO. In parallel, various designs based on fs lasers were proposed to utilize the advantages of fs pulses. CARS microscopy with a single broadband source through optical pulse shaping was demonstrated. CARS micro spectroscopy and imaging with a laser-pumped photonic crystal fiber has been extensively explored. However, high-speed and high-quality images were still difficult to be obtained with these methods. Moreover, it is difficult to perform multimodality imaging on these platforms.

The current teachings couple CARS microscopy to a widely used multiphoton imaging platform based on an fs laser, a synchronously pumped fs OPO, and a PPLN doubling crystal. This method provides a cost-efficient way to maximize the bioimaging capabilities of NLO microscopy. It also offers several advantages over multimodal imaging with two synchronized ps lasers. First, all the pulses are inherently synchronized, which eliminates the need for day-to-day alignment of temporal overlapping of the two beams for CARS imaging. Second, all the wavelengths are in the near IR region from 700 nm to 1.3 μm, an effective window for tissue imaging. Third, the fs pulses allow efficient generation of TPF, SHG, and THG signals. Also, unlike amplified fs lasers, the high repetition rate pulses in the system 100 permit high-speed imaging. Although the highest acquisition rate of the exemplary microscope used in the system of FIG. 1a is 2 μs/pixel, video rate imaging using advanced scanning configurations is feasible due to the large NLO signal level.

Furthermore, the three-beam modality with tunable ability allows background free CARS imaging time-resolved detection.

Furthermore, the three-beam configuration allows background-free CARS imaging of C-D bonds by controlling the polarization of incident beams. Being different from two-beam polarization CARS, no polarization analyzer is needed in the three-beam method. Because the CARS polarization is significantly scrambled after the signal collection optics, two-beam polarization CARS is generally not applicable to a laser-scanning microscope. Such a problem is effectively overcome by polarization control of three incident laser beams. Because both the fs laser and the OPO are tunable, the system 100 also provides the background-free detection of other molecular vibrations. It should be noted that several other methods have been developed for suppression of nonresonant background using a three-beam configuration. Three-color fs pulses were used for time-resolved CARS imaging. In this method, the background removal efficiency is challenged by the broadening of fs pulses through microscope optics. In a recent work by Xie and coworkers, three ps beams were used to acquire on- and off-resonance CARS signals at each pixel. Theoretically such a method would have a better vibrational imaging sensitivity because of the use of ps pulses. However, it is not optimal for other modalities of NLO imaging. The demonstrated three-color polarization CARS imaging presents an example of performing advanced NLO microscopy on a multimodality setup.

Compared with ps lasers, a disadvantage associated with fs lasers is the higher peak power at the focus. It was shown that the photo damage in CARS microscopy increases with shorter wavelengths. In the system 100, the average power of the 1018 nm beam at the sample is relatively low (2.2 mW), and thus a higher power (10 to 20 mW) of 790 nm beam is used. Increasing the power of the Stokes beam by intracavity doubling would be beneficial to increase the photodamage threshold and further enhance the vibrational contrast by minimizing the two-photon resonance enhancement of nonresonant background.

Therefore, multimodality NLO imaging has been disclosed based on a turnkey fs laser, an fs OPO, and a frequency doubling system. The system 100 provides am efficient solution to add CARS and THG imaging modalities to a widely used multiphoton microscope. The integration of CARS, SHG, THG, and multiphoton fluorescence on the same microscope platform greatly enhances the capability, applicability, and versatility of NLO microscopy.

It will be appreciated that various of the above-disclosed and other features, and functions, or alternatives thereof, may be desirably combined into many other different systems or applications. A few of the alternative implementations may comprise various combinations of the methods and techniques described. Various presently unforeseen or unanticipated alternatives, modifications, variations, or improvements therein may be subsequently made by those skilled in the art, which are also intended to be encompassed by the following claims.

The invention claimed is:
1. A method for imaging a sample, the method comprising:
  providing a foundation femtosecond laser beam;
  generating a first femtosecond laser beam and a separate second femtosecond laser beam corresponding to the foundation femtosecond laser beam;
  combining the first femtosecond laser beam and the foundation femtosecond laser beam to generate a first combination femtosecond laser beam;

exposing the sample to the first combination femtosecond laser beam, so that the sample produces an optical signal;

generating a coherent anti-Stokes Raman scattering (CARS) signal by filtering the optical signal using a first filter; and generating a two-photon fluorescence (TPF) signal by filtering the optical signal using a second, different filter.

2. A method for imaging a sample, the method comprising:
providing a foundation femtosecond laser beam;
generating a first femtosecond laser beam and a separate second femtosecond laser beam corresponding to the foundation femtosecond laser beam;
combining the first femtosecond laser beam and the foundation femtosecond laser beam to generate a first combination femtosecond laser beam;
exposing the sample to the first combination femtosecond laser beam, so that the sample produces an optical signal;
generating a coherent anti-Stokes Raman scattering (CARS) signal by filtering the optical signal using a first filter; and
generating a second harmonic generation (SHG) signal by filtering the optical signal using a second, different filter.

3. A method for imaging a sample, the method comprising:
providing a foundation femtosecond laser beam;
generating a first femtosecond laser beam and a separate second femtosecond laser beam corresponding to the foundation femtosecond laser beam;
combining the first femtosecond laser beam and the foundation femtosecond laser beam to generate a first combination femtosecond laser beam;
combining the second femtosecond laser beam with the first combination femtosecond laser beam to generate a second combination femtosecond laser beam;
exposing the sample to the second combination femtosecond laser beam, so that the sample produces an optical signal;
generating a coherent anti-Stokes Raman scattering (CARS) signal by filtering the optical signal using a first filter; and
generating a polarization-sensitive coherent anti-Stokes Raman scattering (PCARS) signal by filtering the optical signal using a second, different filter.

4. The method of claim 3, further comprising:
generating a second harmonic generation (SHG) signal by filtering the optical signal using a third, different filter.

5. The method of claim 3, further comprising:
generating a third harmonic generation (THG) signal by filtering the optical signal using a fourth, different filter.

6. The method of claim 1, further comprising generating the second femtosecond laser beam using an Optical Parametric Oscillator (OPO).

7. The method of claim 1, wherein the foundation laser beam has a wavelength of about 790 nm, the first femtosecond laser beam has a wavelength of about 1018 nm, and the second femtosecond laser beam has a wavelength of about 1290 nm.

8. The method of claim 1, wherein the generating the first femtosecond laser beam further includes generating a third femtosecond laser beam and doubling the frequency of the third femtosecond laser beam to generate the first femtosecond laser beam.

9. The method of claim 8, further comprising generating the third femtosecond laser beam using a periodically poled lithium niobate (PPLN) crystal-based doubler.

10. The method of claim 8, further comprising:
adjusting polarization of the foundation femtosecond laser beam and polarization of the second femtosecond laser beam corresponding to polarization of the third femtosecond laser beam.

11. A multimodal nonlinear optical microscopy platform, comprising:
a laser beam generator configured to provide a foundation femtosecond laser beam;
a splitter configured to provide a first laser beam and a separate second laser beam from the foundation femtosecond laser beam;
a nonlinear optical component configured to generate a first femtosecond laser beam and a separate second femtosecond laser beam from the first laser beam; and
a first combiner operably coupled to combine the second laser beam with the first femtosecond laser beam to generate a first combination femtosecond laser beam;
an objective configured to expose a sample to the first combination femtosecond laser beam, so that the sample produces an optical signal;
a first filter configured to filter the optical signal to provide a coherent anti-Stokes Raman scattering signal; and
a second, different filter configured to filter the optical signal to provide a two-photon fluorescence (TPF) signal.

12. A multimodal nonlinear optical microscopy platform, comprising:
a laser beam generator configured to provide a foundation femtosecond laser beam;
a splitter configured to provide a first laser beam and a separate second laser beam from the foundation femtosecond laser beam;
a nonlinear optical component configured to generate a first femtosecond laser beam and a separate second femtosecond laser beam from the first laser beam; and
a first combiner operably coupled to combine the second laser beam with the first femtosecond laser beam to generate a first combination femtosecond laser beam;
an objective configured to expose a sample to the first combination femtosecond laser beam, so that the sample produces an optical signal;
a first filter configured to filter the optical signal to provide a coherent anti-Stokes Raman scattering signal; and
a second, different filter configured to filter the optical signal to provide a second harmonic generation (SHG) signal when applied to a microscopy sample.

13. A multimodal nonlinear optical microscopy platform, comprising:
a laser beam generator configured to provide a foundation femtosecond laser beam;
a splitter configured to provide a first laser beam and a separate second laser beam from the foundation femtosecond laser beam;
a nonlinear optical component configured to generate a first femtosecond laser beam and a separate second femtosecond laser beam from the first laser beam;
a first combiner operably coupled to combine the second laser beam with the first femtosecond laser beam to generate a first combination femtosecond laser beam;
a second combiner for combining the second femtosecond laser beam with the first combination femtosecond laser beam to generate a second combination femtosecond laser beam;
an objective configured to expose a sample to the second combination femtosecond laser beam, so that the sample produces an optical signal;

a first filter configured to filter the optical signal to provide a coherent anti-Stokes Raman scattering signal; and a second, different filter configured to filter the optical signal to provide a polarization-sensitive coherent anti-Stokes Raman scattering (PCARS) signal.

14. The multimodal nonlinear optical microscopy platform of claim 13, further including a third, different filter configured to filter the optical signal to provide a second harmonic generation (SHG) signal.

15. The multimodal nonlinear optical microscopy platform of claim 13, further including a fourth, different filter configured to filter the optical signal to provide a third harmonic generation (THG) signal.

16. The multimodal nonlinear optical microscopy platform of claim 11, wherein:

the foundation laser beam has a wavelength of about 790 nm, the first femtosecond laser beam has a wavelength of about 1018 nm, and the second femtosecond laser beam has a wavelength of about 1290 nm.

17. The multimodal nonlinear optical microscopy platform of claim 11, wherein the nonlinear optical component is configured to provide a third femtosecond laser beam and further includes a frequency doubling component for doubling the frequency of the third femtosecond laser beam to generate the first femtosecond laser beam.

18. The multimodal nonlinear optical microscopy platform of claim 17, wherein:

the frequency doubling component is a periodically poled lithium niobate (PPLN) crystal-based doubler.

19. The multimodal nonlinear optical microscopy platform of claim 17, further comprising:

a first polarization adjustment component for adjusting polarization of the foundation femtosecond laser beam corresponding to the polarization of the third femtosecond laser beam; and a second polarization adjustment component for adjusting polarization of the second femtosecond laser beam corresponding to the polarization of the third femtosecond laser beam.

* * * * *